US00PP36364P2

(12) United States Plant Patent
Peterse

(10) Patent No.: US PP36,364 P2
(45) Date of Patent: Dec. 31, 2024

(54) ***HELIOPSIS* PLANT NAMED 'VAR006'**

(50) Latin Name: *Heliopsis helianthoides*
Varietal Denomination: VAR006

(71) Applicant: Nova Perenne BV, Zuidwolde (NL)

(72) Inventor: Arie Peterse, Noordwijk (NL)

(73) Assignee: NOVA PERE N NE BV, Zuidia/Olde (NL)

( * ) Notice: Subject to any disclaimer, the term of this patent is extended or adjusted under 35 U.S.C. 154(b) by 0 days.

(21) Appl. No.: 18/657,594

(22) Filed: May 7, 2024

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 6/14; A01H 5/02
See application file for complete search history.

*Primary Examiner* — Keith O. Robinson
(74) *Attorney, Agent, or Firm* — Penny J. Aguirre

(57) ABSTRACT

A new cultivar of *Heliopsis* plant named 'VAR006' that is characterized by its short plant height, its production of many shoots, and its floriferous blooming habit.

3 Drawing Sheets

Botanical classification: *Heliopsis helianthoides.*
Variety denomination: 'VAR006'.

BACKGROUND OF THE INVENTION

The present invention relates to a new and distinct cultivar of *Heliopsis* plant, botanically known as *Heliopsis helianthoides* 'VAR006' and will be referred to hereinafter by its cultivar name, 'VAR006'.

'VAR006' originated as a seedling that arose from seed planted from open pollination of *Heliopsis* 'Loraine Sunshine' (U.S. Plant Pat. No. 10,690) in August of 2021. 'VAR006' was selected as a single unique plant in August of 2021 from amongst the resulting seedlings.

Asexual propagation of the new cultivar was first accomplished by the Inventor by tissue culture using meristematic tissue in January 2022 in Heerhugowaard, The Netherlands. Asexual propagation by tissue culture and stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'VAR006' as unique from and all other varieties of *Heliopsis* known to the Inventor.

1. 'VAR006' exhibits a short plant height.
2. 'VAR006' exhibits production of many shoots.
3. 'VAR006' exhibits a floriferous blooming habit.

The female parent plant differs from 'VAR006' in having a much taller plant height, less shoot production, and a less floriferous blooming habit. 'VAR006' can also be compared to *Heliopsis* cultivars 'Sunburst' (not patented) and 'Sunstruck' (U.S. Plant Pat. No. 25,524). Both 'Sunburst' and 'Sunstruck' are both similar to 'VAR006' in having variegated foliage. 'Sunburst' differs from 'VAR006' in having a taller plant height and less shoot production. 'Sunstruck' differs from 'VAR006' in having leaves that are more carinate and concave in aspect and darker in color due to having darker veins and flowers that are darker yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by De Vroomen Garden Products, Must Have Perennials, Phoenix Perennials Mail Order, Facebook, Pioneer Gardens Inc., Griffin Greenhouse Supplies, LinkedIn, FlorAccess, X, Pintrest, Instagram, Hogendoorn, Kiralykert, Royal Garden Flower Bulbs, Garden Treasures, and Matt Buckingham Photography.

BRIEF DESCRIPTION OF THE DRAWINGS

The accompanying color photographs illustrate the overall appearance and distinct characteristics of the new cultivar. The photographs were taken of a 7-month-old plant as grown in a 15-liter container outdoors in Heerhugowaard, The Netherlands.

The photograph in FIG. 1 provides a side view of a plant of 'VAR006' in bloom.

Figure 1:
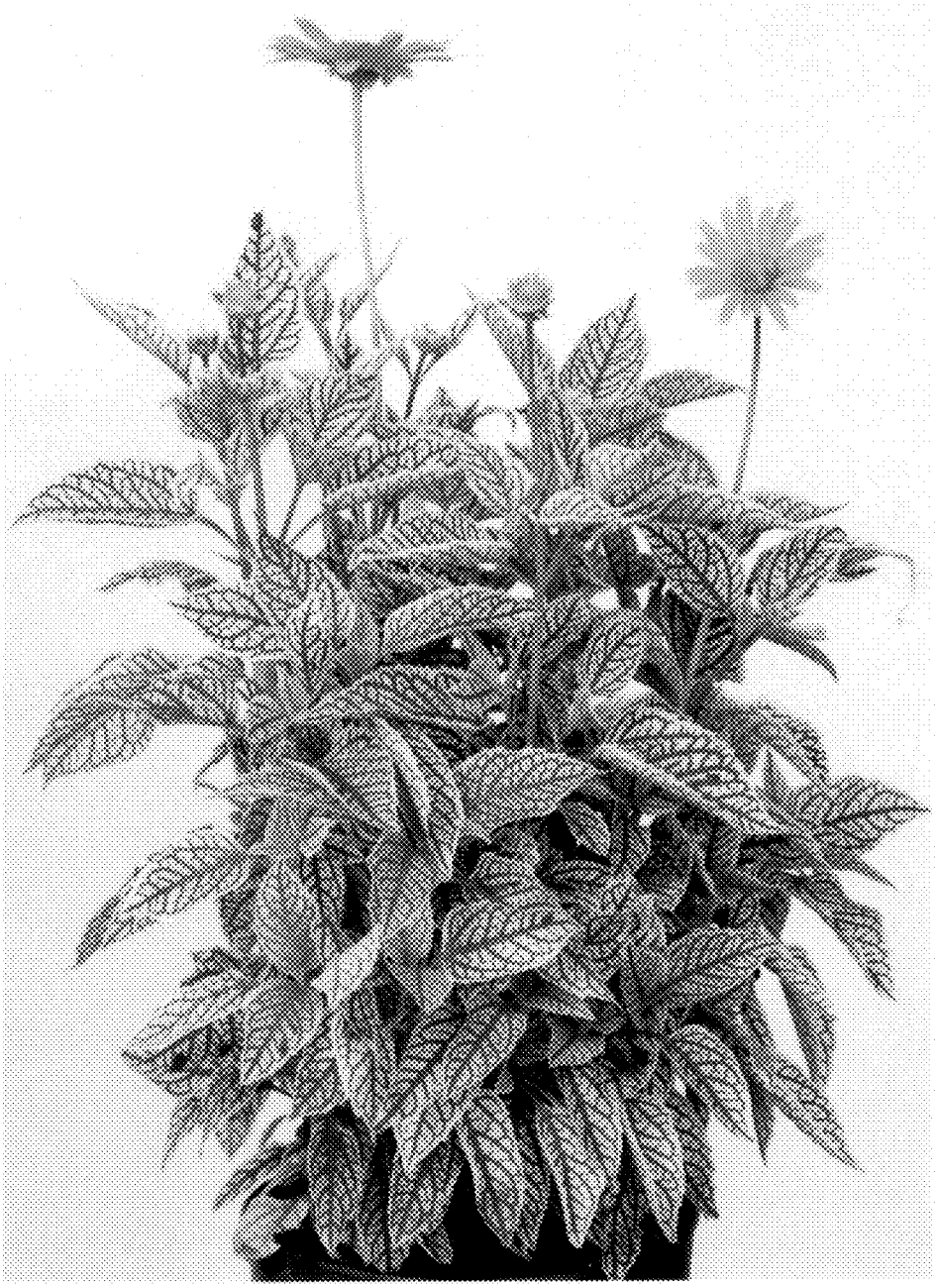
Figure 2:
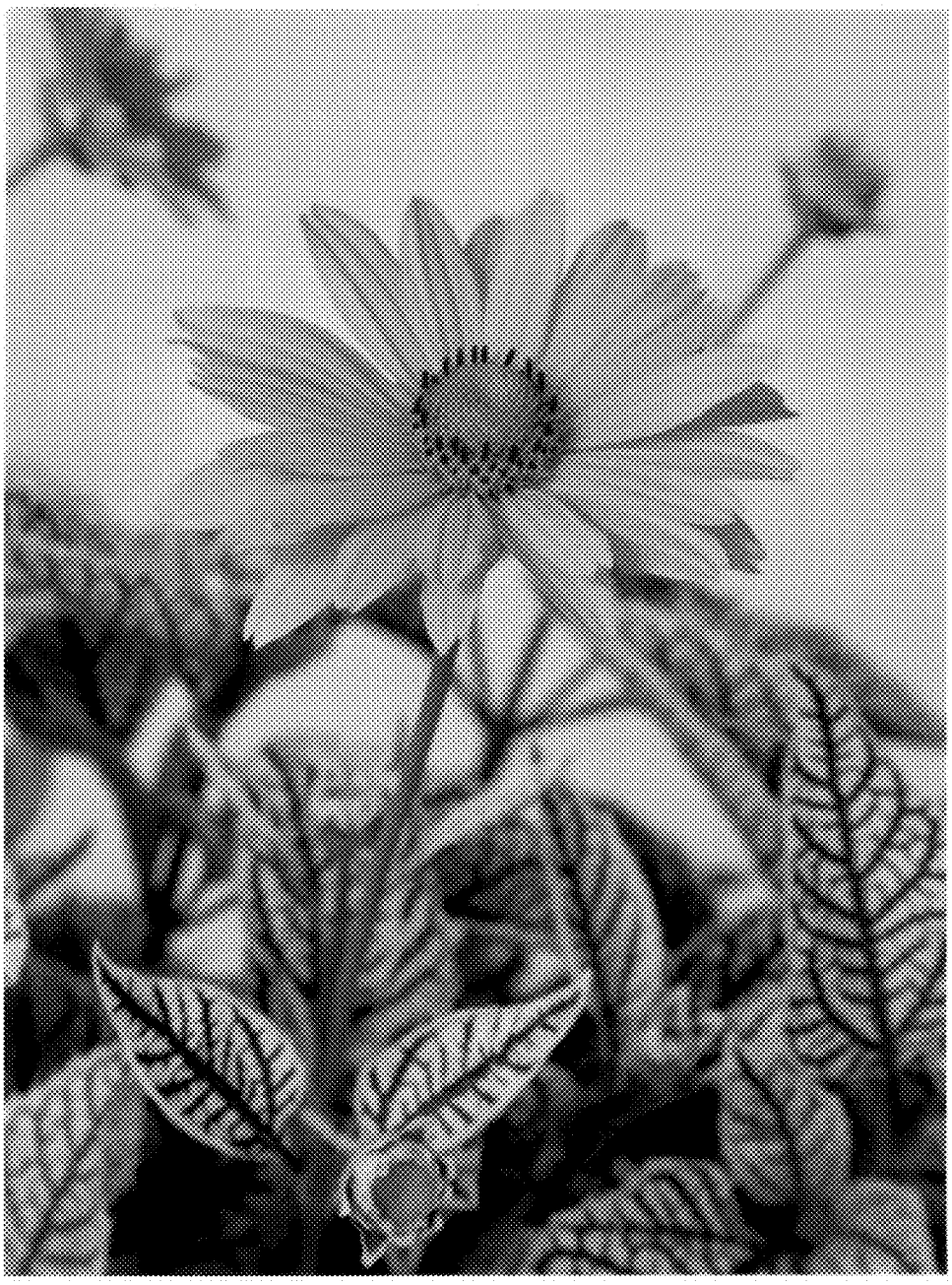

The photograph in FIG. 2 provides a close-up view of an inflorescence of 'VAR006'.

Figure 3:
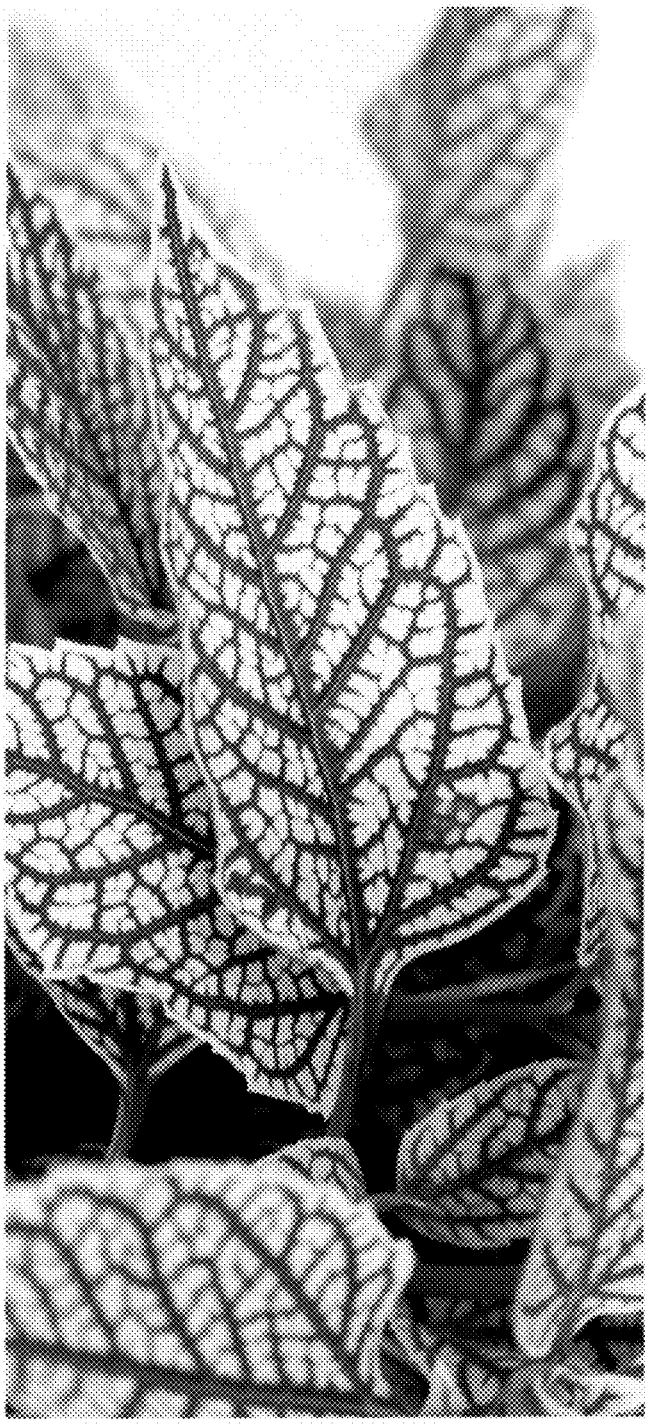

The photograph in FIG. 3 provides a close-up view of the foliage of 'VAR006'.

The colors in the photographs may differ slightly from the color values cited in the detailed botanical description, which accurately describe the colors of the new *Heliopsis.*

DETAILED BOTANICAL DESCRIPTION

The following is a detailed description of the new cultivar as observed on 7-month-old plants of 'VAR006' as grown outdoors in 15-cm containers in Heerhugowaard, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming season*.—Late summer, July into September in The Netherlands.

*Plant type*.—Herbaceous perennial.

*Plant shape*.—Ovate to oblong.

*Plant habit*.—Upright to narrowly spreading.

*Height and spread*.—Average of 50 cm in height and 40 cm in spread as grown in the landscape.

*Hardiness*.—At least in U.S.D.A. Zones 4 to 9.

*Diseases and pests*.—No susceptibility or resistance to diseases or pests has been observed.

*Root description*.—Fibrous.

*Propagation*.—Stem cuttings and tissue culture.

*Root development*.—Time required for root initiation for cuttings is 6 weeks, time required to produce a fully rooted cutting is 9 weeks.

*Growth rate*.—Moderate.

Branch description:

*Branch shape*.—Rounded.

*Branch aspect*.—Main stems; 15° to vertical, secondary; 32.5° to main stem.

*Branch strength*.—Moderate.

*Branch color*.—Young; 146A to 146B, mature; a blend of 144A to 144B, internodes 144B.

*Branch surface*.—Young; sparsely to moderately pubescent with hairs 0.4 mm in length and too small to measure color, mature; glabrous.

*Branch size*.—Average of 25.4 cm in length (excluding inflorescence), 3.5 mm in diameter.

*Quantity*.—Main; 20, lateral 6.

*Internode length*.—Average of 7 cm.

*Branching*.—Freely branched with basal and lateral branches.

Foliage description:

*Leaf division*.—Simple.

*Leaf shape*.—Ovate to nearly deltoid, slightly carinate.

*Leaf base*.—Broadly obtuse with a short acuminate base.

*Leaf apex*.—Acute.

*Leaf margin*.—Serrate, slightly coarsely undulate.

*Leaf venation*.—Pinnate, upper surface 146C to 146D, lower surface 138B.

*Leaf attachment*.—Petiolate.

*Leaf arrangement*.—Opposite.

*Leaf surface*.—Both surfaces rough to the touch moderately covered with strigose pubescence; 0.3 mm in length, color matches leaf surfaces.

*Leaf color*.—Young upper and lower surface; variegated, a blend of 150D and 160D, margins; tinged 68D, veins; 143B, mature upper surface; variegated, a blend of 150D and 157A with areas adjacent to veins 137A, mature lower surface; variegated, 150D with areas adjacent to veins 138A.

*Leaf size*.—Average of 8 cm in length and 4.25 cm in width.

*Petiole*.—2.3 cm in length, 2 mm in diameter, upper surface; moderately glossy, both surfaces 145A in color.

Flower description:

*Inflorescence type*.—Terminal and axillary inflorescences (capitulae), capitula consisting of a receptacle, disc florets and ray florets.

*Lastingness of inflorescence*.—About 5 weeks, persistent.

*Fragrance*.—None.

*Quantity of inflorescences*.—3 inflorescences or buds per lateral branch, 360 inflorescences or buds per plant.

*Inflorescence longevity*.—Average of 10 days.

*Inflorescence buds*.—2.5 cm in depth, 1.7 cm in diameter, flattened globular in shape, matte surface is moderately to densely pubescent, 0.3 mm in length, matches surface color, color; immature ray florets a blend of 153D and 160A, immature disc florets 17B to 17C, immature involucral bracts 143A, base 146D, margins 154D.

*Inflorescence size*.—About 2.3 cm in depth, 7.2 cm in diameter, diameter of disk is 2 cm.

*Receptacle*.—Triangular, 6 mm in depth, 7 mm in diameter, 155C in color.

*Peduncle*.—Round, upright, strong, 144B and 144C in color, surface very slightly glossy and moderately covered with very short hairs; 0.4 mm in length and 157D in color.

*Involucral bracts*.—3 rows, 28 per inflorescence, outer row; 1.1 cm in length, 5 mm in width, ovate in shape, inner row; 6 mm in length, 3 mm in width, obovate in shape, both surfaces matte and pubescent with hairs 0.2 mm in length with color matching surface color, acute apex, broadly cuneate base, entire margins, color; opening and fully open upper surface 147D, top 150D, opening and fully open lower surface 146B, 150D and 154D.

*Disc floret bracts*.—Placed spirally on disc, one bract next to each individual disc floret, 7.5 mm in length, 1.5 mm in diameter, oblanceolate in shape, acute apex, narrow cuneate base, surface smooth, glabrous, and slightly glossy, color; apex 17A, midsection and base 157D.

Ray florets:

*Number*.—Average of 25.

*Arrangement*.—Rotate around disc, 2 whorls.

*Appearance*.—Smooth, glabrous, slightly carinate.

*Shape*.—Elliptic.

*Aspect*.—Nearly horizontal to slightly upward in an average angle of 10° from horizontal.

*Size*.—Average of 3.3 cm in length, 9.5 mm in width.

*Petal apex*.—Praemorse.

*Petal base*.—Attenuate.

*Petal margins*.—Entire.

*Petal texture*.—Upper surface; very slightly glossy, smooth, glabrous, velvety, lower surface; matte, smooth, glabrous, slightly velvety.

*Petal color*.—When opening upper surface; 14A, base 17B, when opening lower surface; 13B, top 11A, fully open upper surface 17B, base 21A, fully open lower surface; 14A, top 11A.

Disc florets:

*Quantity*.—Average of 200.

*Shape*.—Tubular, lower 87.5% free, upper 12.5% free.

*Arrangement*.—Spirally placed on disc, 10 rows.

*Disc lobe apex*.—Acute.

*Disc lobe margin*.—Entire.

*Petal base*.—Fused into tube.

*Petal texture*.—Both surfaces glabrous and slightly glossy.

*Size*.—Average of 7.5 mm in length and 1.5 mm in width.

*Color*.—When opening upper and lower surface; 15A, mid-section and base 150D, when fully open upper and lower surface; 17A, mid-section and base 153D.

Reproductive organs:

*Presence*.—Disc flowers are perfect, ray flowers are carpellate.

*Gynoecium*.—Pistils; 1 per disc and ray floret, 7 mm in length, stigmas; cleft, 3 mm in diameter, 23A in color, styles; 6 mm in length, 157D in color, ovary; 157B in color.

*Androecium*.—Stamens; 5 per disc floret, filaments; 4 mm in length, 153D in color, anthers; narrow oblong in shape, 3 mm in length, 0.5 mm in width, 200A and 200B in color, pollen; low in quantity and 24A in color.

*Fruit and seed*.—No fruits or seeds observed to date.

It is claimed:

1. A new and distinct cultivar of *Heliopsis* plant named 'VAR006' as herein illustrated and described.

* * * * *